United States Patent [19]
Schiller

[11] Patent Number: 5,312,899
[45] Date of Patent: May 17, 1994

[54] DERMORPHIN ANALOGS

[75] Inventor: Peter W. Schiller, Montreal, Canada

[73] Assignee: BioChem Pharma, Inc., Laval, Canada

[21] Appl. No.: 374,521

[22] Filed: Jun. 30, 1989

[30] Foreign Application Priority Data

Jun. 30, 1988 [CA] Canada ............................ 570874

[51] Int. Cl.$^5$ ...................... A61K 37/02; C07K 5/08; C07K 5/10; C07K 7/06
[52] U.S. Cl. .................................... 530/331; 530/330
[58] Field of Search ................... 514/18; 530/330, 331

[56] References Cited

U.S. PATENT DOCUMENTS 4,350,627 9/1982 de Castiglione et al. ..... 260/112.5 E
4,428,938 1/1984 Kisfaludy et al. ................. 424/177

FOREIGN PATENT DOCUMENTS

WO86/02079 4/1986 PCT Int'l Appl. ............ C07K 5/10

OTHER PUBLICATIONS

T. Sato et al., "Opioid Activities of D-Arg$^2$-Substituted Tetrapeptides", *J. Pharmacol. Exp. Ther.*, 242(2), pp. 654-659 (1987).
P. W. Schiller et al., "A Novel Cyclic Opioid Peptide Analog Showing High Preference for μ-Receptors", *Biochem. and Biophys. Res. Commun.*, 127(2), pp. 558-564 (1985).
W. A. Banks and A. J. Kastin, "Peptides and the Blood-Brain Barrier: Lipophilicity as a Predictor of Permeability", *Brain Res. Bull.*, 15, pp. 287-292 (1985).
J. DiMaio, et al., "Synthesis and Pharmaceutical Characterization In Vitro of Cyclic Enkephalin Analogues . . .," *J. Med. Chem.*, 25, pp. 1432-1438 (1982).
S. H. Ferreira and M. Nakamura, "Prostaglandin Hyperalgesia: The Peripheral Analgesic Activity of Morphine, Enkephalins and Opioid Antagonists", *Prostaglandins*, 18, pp. 191-200 (1979).
R. L. Follenfant, et al., "Antinociceptive Effects of the Novel Opioid Peptide BW443C Compared with Classical Opiates; Peripheral Versus Central Actions", *Br. J. Pharmacol.*, 93, pp. 85-92 (1988).
G. W. Hardy, et al., "Peripherally Acting Enkephalin Analogues. 1. Polar Pentapeptides", *J. Med. Chem.*, 31, pp. 960-966 (1988).
J. A. H. Lord, et al., "Endogenous Opioid Peptides: Multiple Agonists and Receptors", *Nature*, 267, pp. 495-499 (1977).
W. R. Martin, et al., "The Effects of Morphine- and Nalorphine-like Drugs in the Nondependant and Morphine-Dependent Chronic Spinal Dog", *J. Pharmacol. Exp. Ther.*, 197, pp. 517-532 (1976).
N. J. W. Russell, et al., "Opiates Inhibit the Discharges of Fine Afferent Units from Inflamed Knee Joint of the Cat", *Neuroscience Lett.*, 76, pp. 107-112 (1987).

(List continued on next page.)

Primary Examiner—Lester L. Lee
Attorney, Agent, or Firm—Fish & Neave

[57] ABSTRACT

Peptides are provided which are suitable for the treatment of pain and gastro-intestinal disorders, such as diarrhea, and are represented by the structure:

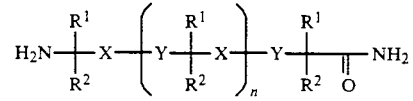

where values for the substituents and n are disclosed herein. Methods for preparing these peptides by solution and solid phase syntheses are also provided. Pharmaceutical compositions utilizing these peptides in a pharmaceutically effective amount and methods of treatment using them are provided.

5 Claims, 6 Drawing Sheets

OTHER PUBLICATIONS

P. W. Schiller, et al., "Unsulfated C-Terminal 7-Peptide of Cholecystokinin: A New Ligand of the Opiate Receptor", *Biochem. Biophys. Res. Commum.*, 85, pp. 1332–1338 (1978) (Schiller I).

P. W. Schiller, et al., "Dermorphin Analogues Carrying an Increased Positive Net Charge . . . ," *J. Med Chem.*, 32, pp. 698–703 (1989) (Schiller II).

R. Schwyzer, "Molecular Mechanism of Opioid Receptor Selection", *Biochem.*, 25, pp. 6335–6342 (1986).

E. Siegmund, et al., "A Method for Evaluating Both Non-Narcotic and Narcotic Analgesics", *Proc. Natl. Exp. Biol. Med.*, 95, pp. 729–731 (1957).

T. W. Smith, et al., "Peripheral Antinociceptive Effects of N-Methyl Morphine", *Life Sci.*, 31, pp. 1205–1208 (1982).

C. Stein, et al., "Antinociceptive Effects of $\mu$- and $\kappa$-agonists in Inflammation are Enhanced by a Peripheral Opioid Receptor-Specific Mechanism", *Eur. J. Pharm.*, 155, pp. 255–264 (1988) (Stein I).

C. Stein, et al., "Peripheral Opioid Receptors Mediating Antinociception in Inflammation. Evidence for Involvement of Mu, Delta and Kappa Receptors", *J. Pharm. Exp. Ther.*, 248, pp. 1269–1275 (1989) (Stein II).

G. Woolfe and A. D. MacDonald, "The Evaluation of the Analgesic Action of Pethidine Hydrochloride (Demerol)", *J. Pharmacol. Exp. Ther.*, 80, pp. 300–307 (1944).

Peptide Hormones, Parsons, ed., Jun. 1976, pp. 1–7.

Inhibitory Effect of H-Tyr-D-Arg-Phe-L-Lys-NH₂ on PBQ-induced Writhing

| Dose mg/kg | No. of Mice | Avg. No. of Writhes | Percent Protection |
|---|---|---|---|
| - | 15 | 25 | - |
| 0.25 | 15 | 18 | 28 |
| 0.375 | 10 | 15 | 40 |
| 0.5 | 15 | 11 | 57 |
| 1.0 | 15 | 7.5 | 70 |
| 2.5 | 15 | 2.5 | 90 |

Evaluation of this collected data resulted in an $ED_{50}$ value of 0.6 mg/kg.

FIG. 1

Antagonist Effect of N-Methyl Levallophane (NML)
on Inhibition PBQ-induced Writhing by
H-Tyr-D-Arg-Phe-Lys-NH$_2$

| Dose mg/kg | No. of Mice | Avg. No. of Writhes | Percent Protection |
|---|---|---|---|
| - | 5 | 28 | - |
| 0.5 | 5 | 25 | 11 |
| 1.0 | 5 | 17 | 40 |
| 2.5 | 5 | 12 | 58 |
| 4.0 | 5 | 1 | 96 |

Evaluation of this collected data resulted in an ED$_{50}$ value of 2.0 mg/kg.

FIG.2

**Inhibitory Effects of
H-Tyr-D-Arg-Phe-Lys-NH$_2$ on PBQ-induced
Writhing and Antagonist Effect of
NML on Inhibition by H-Tyr-D-Arg-Phe-Lys-NH$_2$**

| Peptide Dose mg/kg | NML Dose mg/kg | No. of Mice | Avg. No. of Writhes | Percent Protection |
|---|---|---|---|---|
| - | - | 15 | 26 | - |
| 200 | - | 30 | 7 | 79 |
| 200 | 10 | 10 | 17 | 28 |

FIG. 3

Binding Assays of Opioid Peptide Analogs

| Compound | [³H]DAGO | | [³H]HSLET | | $K_i^\delta/K_i^\mu$ |
|---|---|---|---|---|---|
| | $K_i^\mu$ | relative potency | $K_i^\delta$ | relative potency | |
| H-Tyr-D-Nva-Phe-Orn-NH$_2$ | 1.2 | 8 | 2200 | 0.0012 | 1880 |
| H-Tyr-D-Nva-Phe-Asn-NH$_2$ | 11.7 | 0.8 | 441 | 0.0057 | 17.7 |
| H-Tyr-D-Nle-Phe-Orn-NH$_2$ | 1.4 | 7 | 2870 | 0.0009 | 2130 |
| H-Tyr-D-Arg-Phe-A$_2$bu-NH$_2$ | 5.7 | 1.6 | 12600 | 0.0002 | 2180 |
| H-Tyr-D-Arg-Phe-Orn-NH$_2$ | 1.2 | 7.8 | 9290 | 0.0003 | 7740 |
| H-Tyr-D-Arg-Phe-Lys-NH$_2$ | 1.7 | 5.6 | 19200 | 0.0001 | 11400 |
| H-Tyr-D-Ala-Gly-Phe(NMe)-Gly-ol (DAGO) | 1.22 | 7.7 | 1280 | 0.002 | 1050 |
| Leu-enkephalin | 9.43 | 1 | 2.5 | 1 | 0.27 |

FIG. 4

Guinea Pig Ileum (GPI) and Mouse Vas Deferens (MVD)
Assay of Opioid Peptide Analogs

| | GPI | | MVD | | MVD/GPI |
|---|---|---|---|---|---|
| | IC$_{50}$ | relative potency | IC$_{50}$ | relative potency | IC$_{50}$ ratio |
| H-Tyr-D-Nva-Phe-Orn-NH$_2$ | 104 | 2.36 | 271 | 0.042 | 2.61 |
| H-Tyr-D-Nva-Phe-Asn-NH$_2$ | 181 | 1.36 | 2210 | 0.0052 | 12.2 |
| H-Tyr-D-Nle-Phe-Orn-NH$_2$ | 168 | 1.46 | 2290 | 0.00498 | 13.6 |
| H-Tyr-D-Arg-Phe-A$_2$bu-NH$_2$ | 257 | 0.96 | 659 | 0.0173 | 2.56 |
| H-Tyr-D-Arg-Phe-Orn-NH$_2$ | 346 | 0.71 | 1090 | 0.0105 | 3.15 |
| H-Tyr-D-Arg-Phe-Lys-NH$_2$ | 338 | 0.73 | 781 | 0.0146 | 2.31 |
| H-Tyr-D-Ala-Gly-Phe(NMe)-Gly-ol (DAGO) | 28 | 8.69 | 950 | 0.012 | 33.6 |
| Leu-enkephalin | 246 | 1 | 11.4 | 1 | 0.0463 |

FIG.5

$K_e$ Values (Naloxone) of Positively Charged Opioid Peptide Analogs in the Guinea Pig Ileum Assay

| Compound | $K_e$ |
|---|---|
| H-Tyr-D-Nva-Phe-Orn-$NH_2$ | 1.55 |
| H-Tyr-D-Nva-Phe-Asn-$NH_2$ | 2.08 |
| H-Tyr-D-Nle-Phe-Orn-$NH_2$ | 1.01 |
| H-Tyr-D-Arg-Phe-$A_2$bu-$NH_2$ | 1.32 |
| H-Tyr-D-Arg-Phe-Orn-$NH_2$ | 1.24 |
| H-Tyr-D-Arg-Phe-Lys-$NH_2$ | 1.17 |
| H-Tyr-D-Ala-Gly-Phe(NMe)-Gly-ol (DAGO) | 0.80 |
| Leu-enkephalin | 1.53 |

FIG. 6

DERMORPHIN ANALOGS

TECHNICAL FIELD OF THE INVENTION

This invention relates to novel peptides of medicinal importance for the treatment of pain and gastro-intestinal disorders, methods for their preparation, pharmaceutically acceptable compositions characterized by those peptides, and methods for treating patients using those compositions. The peptides of this invention are characterized by a high degree of selectivity for the $\mu$-opioid receptor. More particularly, the peptides of this invention exhibit superior specificity for the $\mu$-opioid receptor when compared with conventional agents. These peptides also possess a high positive charge or polar character, making them sparingly lipid soluble. Thus, they do not readily permeate the blood-brain barrier. As will be appreciated by the disclosure to follow, the peptides of this invention are particularly well-suited for administration as peripherally acting analgesic and anti-diarrheal agents.

BACKGROUND OF THE INVENTION

A large number of endogenous peptides found in various regions of the central nervous system exhibit opioid activity. This activity is elicited by compounds, known as opiates, which are described as substances which bind to opioid receptors. Concomitant with the multitude of peptides which demonstrate opioid activity was the pharmacological discovery of the existence of multiple opioid receptors. See W. Martin et al., *J. Pharmacol. Exp. Ther.*, 197, p. 517 (1975); and J. Lord et al., *Nature (London)*, 257, p. 495 (1977). Three different types of receptors have been identified. The first, $\delta$, shows a differentiating affinity for enkephalin. The second, $\mu$, shows an enhanced selectivity to morphine and other poly-cyclic alkaloids. The third, $\kappa$, exhibits equal affinity for either group of these ligands and preferential affinity for dynorphin. $\beta$-endorphin appears to bind equally to the $\mu$ and $\delta$ receptors. In general, the $\mu$ receptors seem to be more involved with analgesic effects, whereas the $\delta$ receptors appear to deal with behavioral effects, although the $\delta$ and $\kappa$ receptors may also mediate analgesia.

The major putative function for opiates is their role in alleviating pain. Other areas where opiates are well-suited for use in treatment are conditions relating to gastro-intestinal disorders (diarrhea), schizophrenia, obesity, blood pressure, convulsions, and where seizure induction may alleviate earning or memory loss.

To date, opiates, opioid peptides, and analogs thereof, have either failed to demonstrate, or have demonstrated a limited degree of specificity and selectivity for the receptor or receptors to which they may bind. The less selective and specific an opiate may be, the greater the chance that increased side effects from the administration of the material will be observed. Since each receptor certain effects are symptomatic when each receptor is triggered. However, when an opiate activates more than one receptor, the biological response profile for each receptor is affected, thereby potentiating a spectrum of side effects which may or may not be adverse. Such adverse side effects include heaviness of the limbs, flush or pale complexion, clogged nasal and sinus passages, dizziness, depression, and the like.

Conventional opiate peptides have been chosen from among enkephalin, endorphin, and dynorphin analogs. Other known opiates are poly-cyclic alkaloid structures such as morphine, naloxone, and levorphanol. It is generally recognized that the degree of complementary affinity between the structural characteristics of an opiate receptor and the ligand which functions as an opiate or opioid peptide, is significant to the determination of receptor selectivity and specificity. However, recent reports indicate that specific interactions of opioid peptides with various membrane compartments may also contribute to the ability of these opiates to selectively interact with specific receptors. See R. Schwyser, *Biochemistry*, 25, p. 6336 (1986).

The term "specificity" refers to the particular or definitive preference of an opiate or opioid peptide for one opioid receptor over another. The term "selectivity" refers to the ability of an opiate or opioid peptide to discriminate among several opioid receptors. For instance, the ratio of binding inhibition constants, $K_i\delta/K_i\mu$, is a value that may be used to measure selectivity. This ratio represents the relationship of the affinities for binding to the $\delta$ and $\mu$ receptor. A higher value for this ratio indicates a greater preference of ligand to bind with the $\mu$ receptor over the $\delta$ receptor. One conventional opioid peptide analog, H-Tyr-D-Ala-Gly-Phe(N-Me)-Gly-ol (DAGO), has been understood to be the most $\mu$ selective opioid peptide analog known to date. This peptide has recorded a $K_i\delta/K_i\mu$ value of 1050. Leu-enkephalin, on the other hand, has recorded a $K_i\delta/K_i\mu$ of 0.2. This fractional value reflects a pronounced affinity for the $\delta$ receptor over the $\mu$ receptor. Thus, it would be desirable for an opiate or opioid peptide to demonstrate an increased value for this binding ratio, thereby generating a greater preference for $\mu$ receptor binding and enhancing the peripherally mediated analgesic effects related to these opiates and opioid peptides.

The class of compounds commonly referred to as analgesics are normally quite hydrophobic and thus are extremely well-suited to permeate lipid membranes, such as the blood-brain barrier. Due to this physical capability, these compounds tend to bind with opioid receptors of the central nervous system in the brain, although not necessarily the same ones. This binding may generate similar side effects to those attributed to conventional opiates, opioid peptide and analogs, although the problems are likely to be of a greater magnitude.

Similarly, the hydrophobic character of conventional opiates and opioid peptides tends to delay their rate of passage through the system. Much effort has been placed on improving the adsorption properties of these compounds and decreasing their capability to transcend the blood-brain barrier. However, since their affinity and solubility is greater for lipid materials than for aqueous fluids of physiological pH, these compounds tend to lodge themselves in the organs and fatty tissue of the body. They tend to remain therein for extended periods of time rather than being excreted from the system. The long term toxicity of many of these compounds is generally uncertain, however any prolonged exposure is likely not to be beneficial.

Recent advances in the field of opioid peptides have been directed towards the stabilization of these peptides against enzymatic or hydrolytic degradation. It would be extremely valuable to stabilize these peptides from proleolytic enzymes in order to improve their pharmocokinetic properties. Enhanced resistance to enzymatic degradation would increase the usefulness of these opioid peptides as therapeutic agents. However, since they only exhibit short half lives in vivo, large amounts of such peptides must typically be administered to a subject in order to achieve the desired effect. Alternatively, smaller quantities may be prescribed to an individual, but more frequent dosages would be required to achieve the same level of potency.

It is desirable that a peptide meet several general criteria in order to be considered for any pharmacological interest. First, a peptide should be resilient to proteolytic degradation. Second, a peptide should elicit an enhanced biological response. Third, a peptide must be safe for human consumption. Fourth, a peptide should be capable of being produced in quantities large enough to perform clinical studies respecting its toxicity and later for commercialization. In the present case, less lipid solubility and greater aqueous solubility are also desirable properties for the peptide to possess, to prevent permeation through the blood-brain interface and to permit rapid excretion of any excess administered peptide and its metabolites. Further, it would be desirable for a peptide to elicit selective and specific receptor binding potential, in order to minimize potential side effects resulting from its ingestion.

Regarding suitable production quantities discussed above, several factors are worthy of consideration. The method of preparing the peptide should preferably be simple, efficient, and economical. That is, the reaction scheme of the method should contain few steps, afford high overall yields, and allow a minimum amount of by-product formation. Moreover, the scheme should preferably utilize inexpensive reagents and materials. In this respect, inexpensive and reproduceable diagnostic and analytical methods should be incorporated into the production scheme where feasible. Further, the method should ensure the optical integrity of the peptide by avoiding reagents that will tend to racemize the reactants and products. A racemic mixture of the desired peptide is not likely to fully exhibit the desired pharmacological response.

The optical integrity of a compound relates to its ability to rotate light. This ability is measured by an instrument known as a polarimeter, which utilizes a zero point reference to base its reading. The degree to which a chemically pure material rotates light indicates its relative optical purity. That is, a material may be chemically pure while being optically inactive or racemic. The amount of activity that is observed from a material is often dependant upon its optical purity. Two enantiomers, although possessing identical chemical formulae, may have completely different biological activities. It is common in medicinal applications for a compound of one optical configuration to exhibit activity and usefulness, while its optical rotamer or complimentary enantiomer demonstrates a different activity or is wholly inert. Thus, where optical configuration is important, optical purity, as well as chemical purity is an important concern.

Conventional opiates and opioid peptides exhibit either no specific and selective binding preference for opioid receptors, or limited specific and selective binding preference for those receptors. Moreover, their hydrophobicity and enhanced lipid solubility have permitted them to cross the blood-brain interface to some extent. Further, the combined effects of these two phenomena not only establish the potential for side effects, particularly adverse side effects, and those side effects are likely to be varied and intensified due to the centrally mediated interactions of the opiate or opioid peptides.

Notwithstanding the efforts placed against these concerns heretofore, there is a need for peptides which exhibit a preference for a specific opioid receptor, especially the μ receptor. It would be desirable to design peptides of less lipid solubility than that of conventional opiates or opioid peptides, so that the blood-brain barrier would be impermeable to these peptides. Further, peptides of high polar character would normally possess a greater tendency to become solublized in aqueous fluids of physiological pH, thereby facilitating their excretion and the passing of their metabolites from the system. It would also be desirable to synthesize these peptides in a simple, efficient, and economical manner to facilitate the preparation of suitable quantities for toxicological studies and commercial supplies while retaining the optical integrity of the desired materials.

SUMMARY OF THE INVENTION

The present invention meets all of the goals described above. Specifically, this invention provides peptides which exhibit a preferential selectivity and specificity for, particularly, the μ-opioid receptor. This invention also provides pharmaceutical compositions characterized by those peptides, for the treatment of pain and gastro-intestinal disorders, such as diarrhea. And this invention provides a method for preparing these peptides in a simple, efficient, and economic fashion that affords the peptides in high yield and in such a way that their optical integrity is maintained.

DETAILED DESCRIPTION OF THE INVENTION

The peptides of the present invention include those represented by the formula:

and pharmaceutically effective salts thereof, wherein R$^1$ is a member selected from the group consisting of hydrogen, C$_1$-C$_7$ branched or unbranched alkyl which may or may not be substituted by amino or guanido, phenyl, hydroxyphenyl, methoxyphenyl, benzyl, hydroxybenzyl, methoxybenzyl, aminobenzyl, amidobenzyl, carboxybenzyl, carboxymethylbenzyl, cyanobenzyl, fluorobenzyl, chlorobenzyl, bromobenzyl, iodobenzyl, mercaptobenzyl, and nitrobenzyl;

$R^2$ is hydrogen, methyl, ethyl; or $R^1$ and $R^2$, taken together with the carbon atom to which they are attached, form a cycloalkyl ring containing 3-5 carbon atoms;

X is selected from the group consisting of C=O, N—H, $CH_2$, —O—, C=S, and —S—;

Y is selected from the group consisting of C=O, N—H, $CH_2$, —O—, C=S, and —S—; or X and Y, taken together, represent an olefin linkage wherein X and Y each have a hydrogen atom attached thereto in a cis or trans configuration; and n is 1-7.

The representations for $R^1$ are typically substituents commonly found among naturally occurring α-amino acids or their configurational enantiomers. Preferred groupings include branched or unbranched alkyl groups, which may or may not be substituted by amino or guanido. Particularly preferred groups include $C_1$-$C_5$ branched or unbranched alkyl groups, which may or may not be substituted by amino or guanido at the terminal carbon atom. One especially preferred group represented by $R^1$ is $C_3$-$C_5$ branched alkyl, which may or may not be substituted at its terminal carbon by the guanido functionality and which possesses the D absolute configuration. Another especially preferred group represented by $R^1$ is $C_1$-$C_5$ unbranched alkyl, which may be substituted at its terminal carbon atom by the amino functionality.

Alternatively preferred groupings for $R^1$ include phenyl or benzyl, which may or may not be substituted by hydroxy, methoxy, amino, amido, carboxy, carboxymethyl, cyano, fluoro, chloro, bromo, iodo, mercapto, or nitro. Particularly preferred alternative groupings include benzyl and hydroxybenzyl.

The absolute configuration of a compound relates to how its substituents are oriented in space about a central atom. This notion becomes significant when coupled with the rigors of chirality. Chirality involves the identity of the substituents about that central atom. Thus, in general, a compound is said to be chiral when four distinctly different groups are bound to a central carbon atom. These groups may be spatially aligned in more than one manner without repeating their individual orientations. That is, a chiral compound may exhibit a mirror image which is also chiral. These mirror images are termed meso configurations, and are each absolute configurations of a chiral compound. In amino acids and related compounds, the absolute configurations are designated L or D, depending on whether the substituents align themselves in a clockwise or counterclockwise fashion, respectively. These designations, however, have no bearing on the direction in which they rotate light or whether or not the compounds rotate light at al The peptides of the present invention exhibit many advantages over conventional opiates and opioid peptides. For example, they demonstrate greater activity than that of other peripherally acting opioid peptide analogs reported to date. Further, the potency of these peptides may be as high as about five times that of previously known peripherally acting enkephalin analogs.

The stability observed by the peptides of the present invention exceeds that of naturally occurring opioid peptides, and is at least equal to that of conventional opioid peptide analogs. Without being bound by theory, we believe that the increased resistance to enzymatic degradation over natural opioid peptides exhibited by the peptides of this invention is due to the introduction of D amino acids into the peptide chains. This switch from L to D amino acids neutralizes the digestion capabilities of many of the ubiquitous peptidases found in the digestive tract. Alternatively, the enhanced stability of the peptides of this invention may also be the result of the introduction of modifications of traditional peptide linkages. For example, the introduction of a thioamide linkage may increase the stability of the peptide. And, enhanced stability may also be evidenced by: the reduction of the amide bond to form a secondary amine linkage, the reduction of an internal ester linkage to yield a ketomethylene linkage, the reversal of the atoms which form an ester or amide linkage, the introduction of an unsaturated linkage, or the placement of an ether or thioether linkage into the peptide backbone in order to circumvent the effect of many proteolytic enzymes known to digest small peptides in the stomach or other digestive organ.

The peptides of this invention elicit increased specificity and selectivity with respect to their binding preferences to opioid receptors. Specifically, the peptides of this invention are characterized by a greater specificity and selectivity for the opiate receptor that is most responsible for analgesic effects—the μ receptor—than that exhibited by conventional analgesics utilized to combat pain caused by conditions and the like.

Conventional opiates, used heretofore to alleviate pain, exhibit general binding characteristics for the entire group of opioid receptors, μ, δ, κ, as a whole. As a result, such conventional agents are typically associated with possible side effects triggered by the ability of those agents to bind to more than one opioid receptor. For example, the $K_i\delta/K_i\mu$ ratio, which illustrates representative binding affinities, may vary greatly depending on the compound being examined. Leu-enkephalin has a recorded value of 0.2 for this binding ratio which indicates a predominance for binding to the δ receptor. One conventional opioid peptide analog, H-Tyr-D-Ala-Gly-Phe(NMe)-Gly-ol (DAGO), has demonstrated a $K_i\delta/K_i\mu$ value of 1050 which indicates a greater preference for μ receptor binding. However, the peptides of the present invention demonstrate a further increase for the values of this ratio. A preferred peptide of this invention, H-Tyr-D-Arg-Phe-Lys-$NH_2$, demonstrated a $K_i\delta/K_i\mu$ value of 11400. This represents at least about a ten-fold enhancement of μ receptor binding over that elicited by the previously known opioid peptides.

The centrally mediated adverse side effects and addictive potential demonstrated by conventional opiates and opioid peptides is not observed by the peptides of this invention. Once administered, the ligand-receptor interactions occur on the neurons of the peripheral nervous system of the brain. These peripherally mediated interactions alleviate the adverse side effects and potential dependency concerns attributed to conventional analgesics.

The peptides of this invention advantageously minimize the side effects associated with conventional analgesics because they tend to bind to specific opiate receptors not found in the central nervous system of the brain. These peptides may carry a high net charge, either positive or negative, which make them very polar. Preferably, the peptides possess a high net positive charge in the range of about +1 or higher. This high polarity allows them to be less solubilized in lipid material and more highly solubilized in aqueous fluids and materials, preferably aqueous fluids of physiological pH. The low hydrophobic character of these peptides minimizes the likelihood that they will permeate the blood-brain barrier. Thus, the peptides act as biological response modifiers peripherally, by binding to $\mu$ receptors located on sensory neurons of the peripheral nervous system. This prevents noxious stimuli from reaching the spinal cord and thereby results in an analgesic effect.

Similarly, since the peptides disclosed herein exhibit decreased lipid solubility and tend not to migrate across the blood-brain barrier, the likelihood of developing a narcotic addiction such as that associated with conventional opiates, is either eliminated or greatly reduced. Thus, the progressively weaker effects that are observed when tolerance builds for an opiate or opioid peptide, or the withdrawal signs associated with dependence or addition, is not a grave concern with the peptides of the present invention.

The peptides of the present invention are also extremely well-suited for use as anti-diarrheal agents. The enhanced stability to proteolytic degradation and decreased affinity for lipid tissues exhibited by these peptides permits them to endure the environment of the gastro-intestinal tract for extended periods of time and greatly reduces their ability to cross the blood brain barrier. This ability to withstand the degradative effect of the ubiquitous enzymes of the digestive tract and to remain in the tract without becoming absorbed into its tissue are two characteristics which render these peptides useful in the treatment of diarrhea.

The peptides of this invention may be prepared by initially reacting a first appropriately protected amino acid with a second appropriately protected amino acid in an organic solvent inert to the reactants, in the presence of a suitable peptide coupling agent according to the following scheme:

wherein Z is a suitable nitrogen protecting group and $R^1$ and $R^2$ are as defined hereinabove. The desired peptides may be prepared by utilizing the appropriate amino acids and repeating this reaction sequence as required until a peptide with three to ten amino acid residues has been prepared. A suitable deprotection method may then be employed to remove specified or all of the remaining protecting groups or the peptide from the resin once the desired peptide has been prepared.

The first appropriately protected amino acid and, for instance, an appropriately protected tyrosine may be reacted together in the presence of a suitable peptide coupling agent in a suitably inert organic solvent with stirring, shaking, or agitation to form a protected tyrosine containing dipeptide. Introducing this dipeptide to appropriate protecting group removal conditions affords a selectively deprotected dipeptide which is well-suited for continued peptide synthesis. Contacting this mono-deprotected tyrosine containing dipeptide with an appropriately protected amino acid having a side chain represented by $R^1$, described hereinabove, in the presence of a suitable peptide coupling agent in a suitably inert organic solvent with stirring, shaking, or agitation forms a protected tyrosine containing tripeptide. This method may be repeated as many times as necessary to achieve the desired peptide.

The method of preparation for peptide synthesis requires specific functional groups to react with other substituents to link amino acid residues in a desired manner to form a peptide possessing a known and desired sequence of amino acid residues. Since amino acids possess at least two reactive functional groups, suitable protection, blocking, or masking of these groups is required to ensure that reaction will occur only at specifically desired sites.

These protecting groups should be introduced to the moiety efficaciously while their removal should be performed under conditions which do not affect other portions of the molecule. In this manner, certain reactions and modifications may be performed on the amino acid, peptide, or other compound, with assurance that the protected functionality will not interfere with the desired reaction. Further, by choosing a protecting group that is sensitive and labile to certain reactive conditions, a reaction scheme may be outlined to advantageously utilize these characteristics to effectively remove the protecting group once the synthesis is complete.

A variety of protecting groups known in the field of peptide synthesis and recognized by conventional abbreviations therein, may be found in T. Greene, *Protective Groups In Organic Synthesis*, Academic Press (1981). Among the preferred protecting groups that may be utilized for suitable protection of reactive nucleophilic substituents include, for example, benzyl (Bz), carbobenzyloxy (Cbz), t-butoxycarbonyl (Boc), or 9-fluorenylmethyloxy-carbonyl (Fmoc).

Coupling of amino acids, which may be the same or different as those described above, to yield small peptides in route to peptides comprised of greater numbers of amino acid residues may be accomplished by employing established techniques in the field of peptide chemistry. A broad range of suitable reactions are described in E. Gross and J. Meinhofer, 4 *The Peptides: Analysis, Synthesis, Biology; Modern Techniques of Peptide and Amino Acid Analysis*, John Wiley & Sons, (1981) and M. Bodanszky, *Principles Of Peptide Synthesis*, Springer-Verlag (1984). The peptide coupling agents which may be used to assist condensation of amino and carboxylic acid moieties include N,N'-dicyclohexylcarbodiimide (DCC), N,N'-carbonyl diimidazole (CDI), 1-hydroxy benzotriazole (HOBt), ethyl chloroformate, benzyl chloroformate, 1-(ethoxycarbonyl)-2-ethoxy-1,2-dihydroquinoline (EEDQ), benzotriazoyl-oxy-tris-(dimethy)amino-phosphonium hexafluoro phosphate (BOP) and the like. A preferred technique uses DCC as the coupling reagent. The DCC method may be used with or without catalytic additives such as 4-dimethylaminopyridine (DMAP), copper (II) chloride or HOBt to hasten the reaction and suppress the racemization of the desired compound.

The DCC reaction is often performed at room temperature but may be carried out from about $-78°$ C. to gentle reflux in a variety of solvents that are inert with respect to the reactants. The solvents are normally organic solvents which are polar and aprotic. Preferred solvents include, for example, dichloromethane, chloroform, diethyl ether, tetrahydroform (THF), N,N'-dimethylformamide (DMF), and the like. Particularly preferred solvents are dichloromethane and DMF. In general, the coupling reaction may be carried out at atmospheric pressure a temperature of $-78°$ C. to reflux for a period of between 1 and 48 hours. Preferably, the reaction is carried out at about $-10°$ C. to $25°$ C. with stirring, shaking or agitation, over a period of between 4 and 6 hours.

An alternative synthetic approach for preparing the peptides of the present invention can be effected via the Merrifield solid phase methodology and its known variants. Thus, a Merrifield resin is prepared by well-known solid phase peptide synthesis methods. A covalently attached α-amino acid residue, attached at its carboxyl functionality or, similarly, a peptide with a free terminal amino functionality may be carried by said resin. Alternatively, said residue may be attached to said resin at its amino functionality. Preferably, this resin is para-methylbenzhydrylamine resin when a peptide amide is desired, although other resins known in the art of solid phase peptide synthesis may also be advantageously employed. Treatment of said resin with appropriately protected amino acids to afford desired amino acid residues in the peptide chain under standard solid phase peptide synthesis conditions affords the desired product.

Once the desired peptide is assembled, the compound so formed may be entirely freed of its protecting groups according to well-known protocols, such as, for example, treatment with liquid hydrogen fluoride (HF). Where, however, the peptide requires selective removal of the protective groups, usually from an amino terminus, suitable reaction conditions must be employed. The Boc protected amino functionality of amino acid derivatives and terminal amines of peptides may be removed, e.g., by treatment with cold trifluoroacetic acid (TFA) at $0°$ C. under suitable atmospheric conditions, e.g., adjusting the pH to between about 8 and 9. Under these conditions, the benzyl, carbobenzyloxy and other protecting groups are left unaffected. The TFA salt of the amino acid derivative or protected peptide may be mixed in a suitable organic solvent and subjected to mild aqueous basic conditions. The organic solution, containing said amino acid derivative or said protected peptide with free amino functionality, may then be dried and concentrated to afford the free amino derivative.

Where Bz or Cbz is utilized as a protecting group, hydrogenation is the appropriate means for effecting the removal of these groups. Hydrogen gas is passed over a solution of the protected material in an alcoholic or other solvent, provided the solvent is not halogenated, and a catalytic amount of a palladium on activated carbon catalyst is added. The hydrogenation vessel is shaken or stirred until a stoichiometric amount of hydrogen has been absorbed and the material has been suitably reduced and freed of its benzyl or carbobenzyloxy protecting groups.

When Fmoc is used as a protecting group for amino acids, peptides or Merrifield resin derivatives, the corresponding free amino group may be generated selectively by treatment with piperidine in DMF under suitable atmospheric and thermal conditions.

By employing liquid HF containing dialkyl sulfide with anisole and thioanisole under suitable conditions at a temperature of $-78°$ C. to $0°$ C., the peptide may be obtained free from all of the individual protecting groups of the component amino acid residues.

The amounts of the reactants utilized in the aforementioned reaction, as well as the conditions required to facilitate reaction and encourage efficient completion may vary widely. However, in general, the amounts of material employed to induce reaction in the processes discussed above will be substantially stoichiometric, unless otherwise specified. In the following examples, reaction concentrations were generally held at 0.1M to the reactants, unless a higher concentration or dilution would be particularly useful for influencing the direction of a specific reaction. In practice, the amounts used will depend upon variations in reaction conditions and the nature of the reactants.

In any of the synthesis methods described above, the desired products may be isolated from the reaction mixture by crystallization. Alternatively, chromatographic techniques including, but not limited to, normal phase, reverse phase, ion-exchange, affinity, or gel permeation, may be employed, as well as electrophoresis or extraction or other means.

Pharmaceutically acceptable salts of the peptides of this invention may be formed conventionally by reaction with an appropriate acid. The addition salts so formed from addition by acid may be identified by hydrochloric, hydrobromic, phosphoric, acetic, fumaric, salicylic, citric, lactic, mandelic, tartaric, oxalic, methanesulphonic, and the like.

The present invention also provides pharmaceutical compositions which comprise a pharmaceutically effective amount of the peptides of this invention, or pharmaceutically acceptable salts thereof, and, preferably, a pharmaceutically acceptable carrier or adjuvant. Therapeutic methods of this invention comprise the step of treating patients in a pharmaceutically acceptable manner with those peptides or compositions. Such compositions may be in the form of tablets, capsules, caplets, powders, granules, lozenges, suppositories, reconstitutable powders, or liquid preparations, such as oral or sterile parenteral solutions or suspensions.

In order to obtain consistency of administration, it is preferred that a composition of the invention is in the form of a unit dose. The unit dose presentation forms for oral administration may be tablets and capsules and may contain conventional expedients. For example binding agents, such as acacia, gelatin, sorbitol, or polyvinylpyrrolidone; fillers, such as lactose, sugar, maize-starch, calcium phosphate, sorbitol or glycine; tabletting lubricants such as magnesium stearate; disintegrants, such as starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixers, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminium stearate gel, or hydrogenated edible fats; emulsifying agents, such as sorbitan monooleate or acacia; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl para-hydroxybenzoate, or n-butyl parahydroxybenzoate or sorbic acid; and, if desired, conventional flavoring or coloring agents.

For parenteral administration, fluid unit dosage forms may be prepared by utilizing the peptide and a sterile vehicle, and, depending on the concentration employed, may be either suspended or dissolved in the vehicle. In preparing solutions, the peptides of this invention may be dissolved in water, whereas opiates used heretofore showed only marginal solubility in aqueous media or physiological fluids. Once in solution, the peptide may be injected and filter sterilized before filling a suitable vial or ampoule and subsequently sealing the carrier or storage package. Adjuvants, such as a local anaesthetic, a preservative or a buffering agent, may be dissolved in the vehicle prior to use. Stability of the pharmaceutical composition may be enhanced by freezing the composition after filling the vial and removing the water under vacuum, e.g., freeze drying the composition. Parenteral suspensions may be prepared in substantially the same manner, except that the peptide should be suspended in the vehicle rather than being dissolved, and, further, sterilization is not achievable by filtration. The peptide may be sterilized, however, by exposing it to ethylene oxide before suspending it in the sterile vehicle. A surfactant or wetting solution may be advantageously included in the composition to facilitate uniform distribution of the peptide.

The pharmaceutical compositions of this invention comprise a pharmaceutically effective amount of a peptide of this invention and a pharmaceutically acceptable carrier. Typically, they contain from about 0.1% to about 99% by weight, preferably from about 10% to about 60% by weight, of a peptide of this invention, depending on which method of administration is employed.

The present invention also provides a method for treatment of pain or diarrhea in patients, such as mammals, including humans, which comprises the step of administering to the patient a pharmaceutically effective amount of a peptide, a pharmaceutically acceptable sat thereof, or a pharmaceutical composition as described above.

The dosage of the peptide used in the treatment will vary, depending on the seriousness of the disorder, the weight of the patient, the relative efficacy of the peptide and the judgment of the treating physician. However, suitable unit dosages in humans may be between about 0.05 mg to about 100 mg. For example, a unit dosage may be from between about 0.2 mg to about 50 mg. Such a unit dosage, described hereinabove, may be administered more than once a day, e g., two or three times a day. Thus, the total daily dosage is in the range of about 0.01 mg to 10 mg/kg. Such therapy may extend for several weeks, in an intermittent or uninterrupted manner, until the patient's symptoms are eliminated.

In order that this invention may be better understood, the following examples are set forth. These examples are for the purposes of illustration only, and are not to be construed as limiting the scope of the invention in any manner.

EXAMPLE 1

Synthesis of
L-tyrosyl-D-arginyl-L-phenylalanyl-L-iysylamlde a) Solution Synthesis i) Preparation of α-N-Cbz-L-tyrosyl-O-benzyl-D-arginine α-N-Cbz-L-tyrosine-O-benzyl ether (8.02 mmol) and D-arginine-t-butyl ester (8.0 mmol) were well dissolved in dichloromethane (21 ml) at 0° C. N,N'-dicyclohexylcarbodiimide (DCC) (8.27 mmol) and 1-hydroxybenzotriazole (HOBt) (8.27 mmol) were added portionwise. The mixture was stirred for 1 hour at constant ice temperature and then filtered. The filtrate was transferred to a separating funnel and washed successively with saturated brine/5% aqueous citric acid and saturated brine/5% aqueous sodium bicarbonate followed by saturated brine alone. The organic phase was then dried, concentrated, and the residue purified by flash chromatography on silica gel employing a 3:1 hexane-ethyl acetate solvent as an eluant to obtain the α-N-Cbz-L-tyrosyl-O-benzyl ether-D-arginine-t-butyl ester as an oil in high yield (93%).

α-N-Cbz-L-tyrosyl-O-benzyl ether-D-arginyl-t-butyl ester was treated with trifluoroacetic acid (TFA) at 0° C. under nitrogen for 0.5 hours. The TFA was removed in vacuo to yield α-N-Cbz-L-tyr-osyl-O-benzyl ether-D-arginine, in quantitive yield, suitable for use in the next step.

Using the procedure described hereinabove and the appropriate starting materials, these additional protected dipeptides were prepared α-N-Cbz-L-tyrosyl-O-benzyl ether-D-norlvaline
α-N-Cbz-L-tyrosyl-O-benzyl ether-D-norleucine
α-N-ϵ-N-di-Cbz-L-lysyl-L-tyrosine-O-benzyl ether ii) Synthesis of α-N-Cbz-L-tyrosyl-O-benzyl ether-D-arginyl-L-phenylalanine α-N-Cbz-L-tyrosyl-O-benzyl ether-D-arganine (7.46 mmol) and L-phenylalanyl-t-butyl ester (7.44 mmol) were well dissolved in dichloromethane (20 ml) at 0° C. DCC (7.69 mmol) and HOBt (7.69 mmol) were added portionwise with stirring. The mixture was allowed to react for 1 hour at constant ice temperature and then filtered. The filtrate was transferred to a separating funnel and washed successively with saturated brine/5% aqueous citric acid and saturated brine/5% aqueous sodium bicarbonate followed by saturated brine alone. The organic phase was then dried, concentrated, and the residue purified by flash chromatography on silica gel employing a 2:1 hexane-ethyl acetate solvent as an eluant to afford the α-N-Cbz-L-tyrosyl-O-benzyl ether-D-arginyl-L-phenylalanyl-t-butyl ester as an oil in high yield (92%).

α-N-Cbz-L-tyrosyl-O-benzyl ether-D-arginyl-L-phenylalanyl-t-butyl ester was treated with trifluoroacetic acid (TFA) at 0° C. under nitrogen for 0.5 hours. The TFA was removed in vacuo to yield α-N-Cbz-L-tyrosyl-O-benzyl ether-D-arginyl-L-phenylalanine, in quantitive yield, suitable for use in the next step.

Using the procedure described hereinabove and the appropriate starting materials, these additional protected tripeptides were prepared α-N-Cbz-L-tyrosyl-O-benzyl ether-D-norvalyl-L-phenylalanine α-N-Cbz-L-tyrosyl-O-benzyl ether-D-norleucyl-L-phenylalanine α-N-ε-N-di-Cbz-L-lysyl-L-tyrosyl-O-benzyl ether-D-arginine.

iii) Synthesis of N-Cbz-L-tyrosyl-O-benzyl ether-D-arginyl-L-phenylalanyl-ε-N-Cbz-L-lysylamide α-N-Cbz-L-tyrosyl-O-benzyl ether-D-arginyl-L-phenylalanine (6.71 mmol) and ε-N-Cbz-L-lysylamide (6.70 mmol) were well dissolved in dichloromethane (18 ml) at 0° C. DCC (6.92 mmol) and HOBt (6.92 mmol) were added in small increments with stirring. The mixture was allowed to react for 1 hour at constant ice temperature and then filtered. The filtrate was transferred to a separating funnel and washed successively with saturated brine/5% aqueous citric acid and saturated brine/5% aqueous sodium bicarbonate followed by saturated brine alone. The organic phase was then dried, concentrated, and the residue purified by flash chromatography on silica gel employing a 1:1 hexane-ethyl acetate solvent as an eluant to afford the α-N-Cbz-L-tyrosyl-O-benzyl ether-D-arginyl-L-phenylalanyl-ε-N-Cbz-L-lysylamide as an oil in high yield (92%).

α-N-Cbz-L-tyrosyl-O-benzyl ether-D-arginyl-L-phenylalanyl-ε-N-Cbz-L-lysylamide was dissolved in methanol, purged with argon, and treated with a catalytic amount of 10% palladium on activated carbon. Hydrogen gas was passed over the system with agitation for 0.5 hours. The mixture was filtered through Celite and the methanol was removed in vacuo to yield L-tyrosyl-D-arginyl-L-phenylalanyl-L-lysylamide in quantitive yield.

Using the procedure described hereinabove and appropriate starting materials, these additional peptides were prepared:

L-tyrosyl-D-norvalyl-L-phenylalanyl-L-ornithylamide

L-tyrosy-D-norleucyl-L-phenylaanyl-L-ornithylamide

L-tyrosyl-D-arginyl-L-phenylalanyl-α, δ-diaminobutyryamide

L-tyrosyl-D-arginyl-L-phenylalanyl-L-ornithylamide

L-lysyl-L-tyrosyl-D-arginylphenyaanyl-L-lysylamide b) Solid Phase Synthesis i) Preparation of α-N-Fmoc-L-phenylalanyl-ε-N-Boc-L-lysyl-resin amide α-N-Fmoc-ε-N-Boc-L-ysine, attached to a para-methylbenzhydrylamine resin at its carboxyl functionality, was treated with a 50% dichloromethane solution of piperidine at room temperature for 30 minutes. The resin was then collected, washed successively with four portions of 10 ml dichloromethane, four portions of 10 ml isopropanol (IPA) and dried for subsequent use.

A solution of α-N-Fmoc-L-phenylalanine (0.948 mmol) in dry DMF (7 ml) was added to ε-N-Boc-L-lysine (0.632 mmol/g of resin), attached by its carboxyl group to a para-methylbenzhydrylamine Merrifield resin, with stirring at 25° C. DCC (0.948 mmol) and HOBt (0.948 mmol) were added portionwise. The reaction was agitated for 1.6 hours after which time another portion of the protected phenylalanine (0.948 mmol) was added and stirring was resumed for 2 hours. The resin was collected, washed with four 10 ml portions of DMF, then four 10 ml portions of IPA and subsequently dried in preparation for further reaction. Completion of the peptide coupling reaction was verified by the ninhydrin test.

ii) Preparation of alpha-N-Fmoc-D-arginyl-L-phenylalanyl-ε-N-Cbz-L-lysyl-resin amide α-N-Fmoc-L-phenylalanyl-ε-N-Boc-L-lysyl-resin amide was treated with a 50% dichloromethane solution of piperdine at room temperature for 30 minutes. The resin was then collected, washed successively with four portions of 10 ml dichloromethane and four portions of 10 ml isopropyl alcohol (IPA) and dried for subsequent use.

A solution of α-N-Fmoc-D-arginine (0.939 mmol) in DMF (7 m) was added to L-phenylalanyl-L-ε-N-Boc-L-lysyl resin amide (0.632 mmol/g of resin) with agitation at 25° C. HOBt (0.939 mmol) and DCC (0.939 mmol) were then added slowly. The reaction was allowed to proceed for 1-2 hours after which time the resin was collected, washed with four 10 ml portions of DMF, four 10 ml portions of IPA, and dried for further reaction. Completion of the peptide coupling reaction was verified by the ninhydrin test.

iii) Preparation of α-N-Fmoc-L-tyrosyl-O-benzyl ether-D-arginyl-L-phenylalanyl-ε-N-Boc-L-lysyl resin amide α-N-Fmoc-D-arginyl-L-phenylalanyl-ε-N-Boc-L-lysyl resin amide was treated with a 50% dichloromethane solution of piperdine at room temperature for 30 minutes. The resin was then collected, washed successively with four portions of 10 ml dichloromethane and four portions of 10 ml IPA and dried for subsequent use.

A solution of α-N-Fmoc-L-tyrosine-O-benzyl ether (0.929 mmol) in DMF (7 ml) was added to D-arginyl-L-phenylalanyl-ε-N-Boc-L-lysyl resin amide (0.929 mmol/g of resin) with agitation at 25° C. DCC (0.929 mmol) and HOBt (0.929 mmol) were added portionwise and the reaction proceeded for 1-2 hours. The resin was then collected, washed with four 10 ml portions of DMF, four 10 ml portions of IPA, and dried for further reaction. Completion of the peptide coupling reaction was verified by the ninhydrin test.

iv) Preparation of L-tyrosyl-D-arginyl-L-phenylalanyl-L-lysylamide by Treatment of the Resin with Liquid HF α-N-Fmoc-L-tyrosyl-O-benzyl ether-D-arginyl-L-phenylalanyl-ε-N-Boc-L-lysyl resin amide was treated with liquid hydrogen fluoride (5 ml) containing anisole, dimethyl sulfide, and thioanisole (0.5 ml 1:1:1 v/v) at 0° C. for 1 hour. After evaporation of the solvent, the residue was dissolved in 10% aqueous acetic acid. The aqueous solution was washed with diethyl ether (30 ml), eluted with water and lyophilized to dryness. The crude peptide was dissolved in 92% aqueous acetic acid (25 ml) and purified first by gel filtration on a Sephadex G 25 column with an acetic acid solvent as the eluant followed by reverse phase chromatography employing a $C_{18}$ packed column with a linear gradient of 1% TFA in 0-80% methanol-water as a solvent.

EXAMPLE 2

Pharmacological Assay of L-tyrosyl-D-arginyl-L-phenylalanyl-L-lysylamide in Mice A group of male CD1 Charles River albino mice (18g-22g) were injected intraperitoneally with 0.3 ml/20 g body weight of a 0.02% solution of 2-phenyl-1,4-benzoquinone (PBQ), according to the procedure described in Siegmund et al., *Proc. Soc. Exp. Biol. Med.*, 95, p. 729 (1957). The writhing and contortional movements of the mice over the following 15 minutes were observed and recorded. Another group of mice were administered L-tyrosyl-D-arginyl-L-phenyl-alanyl-L-lyslamide (H-Tyr-D-Arg-Phe-Lys-$NH_2$) 20 minutes prior to injection with PBQ. The average number of writhes was established and the percent inhibition of writhing movements was calculated. An $ED_{50}$ was established to be 0.6 mg/kg using a regression-line method. The $ED_{50}$ was defined as that dosage of drug which reduced by half the number of writhes obtained in PBQ challenged mice after vehicle administration.

Figure 1:
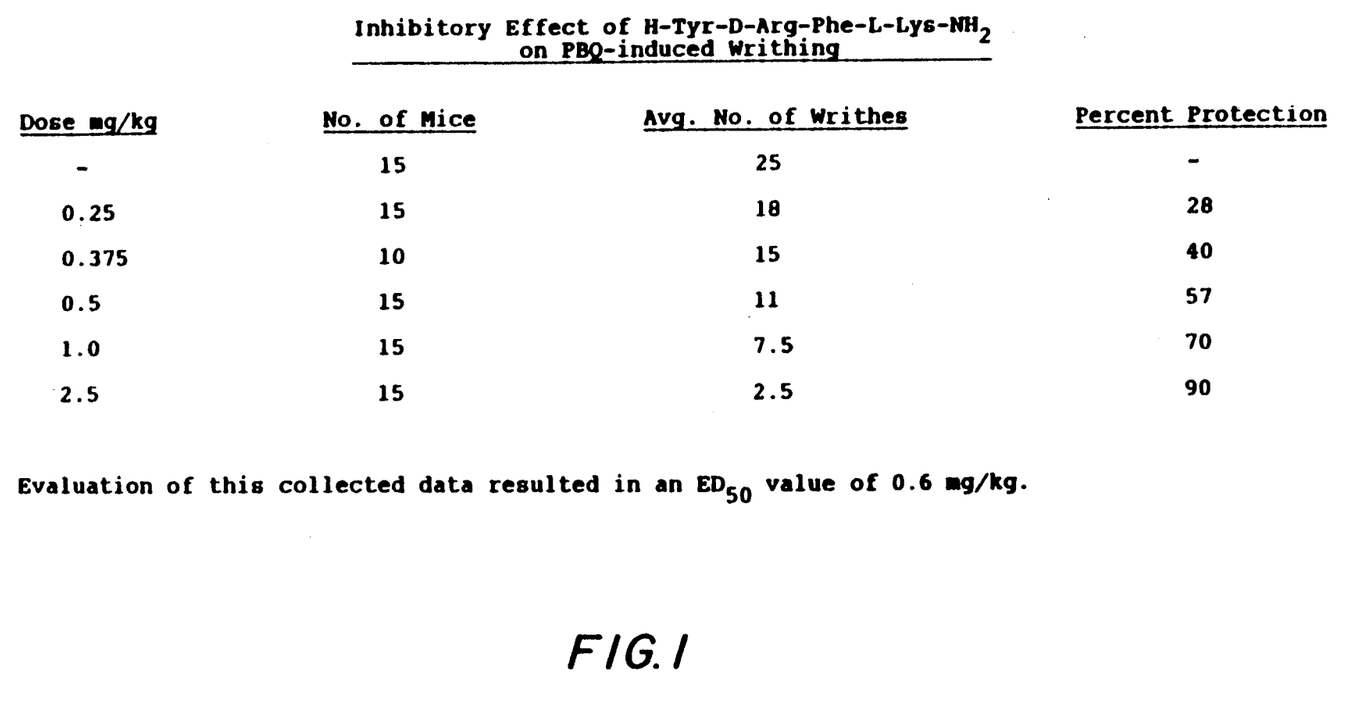
FIG. 1 is a table measuring the inhibitory effect of H-Tyr-D-Arg-Phe-L-Lys-NH$_2$ on PBQ-induced writhing.

The analgesic effects of H-Tyr-D-Arg-Phe-Lys-$NH_2$, when examined by the PBQ writhing test, produced a dose-dependant inhibition of the writhing movements (see FIG. 1, infra). This result indicated that H-Tyr-D-Arg-Phe-Lys-$NH_2$ produced an increased anti-nociceptive activity. The analgesic potency of H-Tyr-D-Arg-Phe-Lys-$NH_2$ was found to be comparable to morphine in a similar assay. See R. Follenfant et al., "Antinociceptive Effects of the Novel Opioid Peptide BW443C compared with Classical Opiates; Peripheral Versus Centra Actions", *Br. J. Pharmacol.*, 93, p. 85 (1988).

Figure 2:
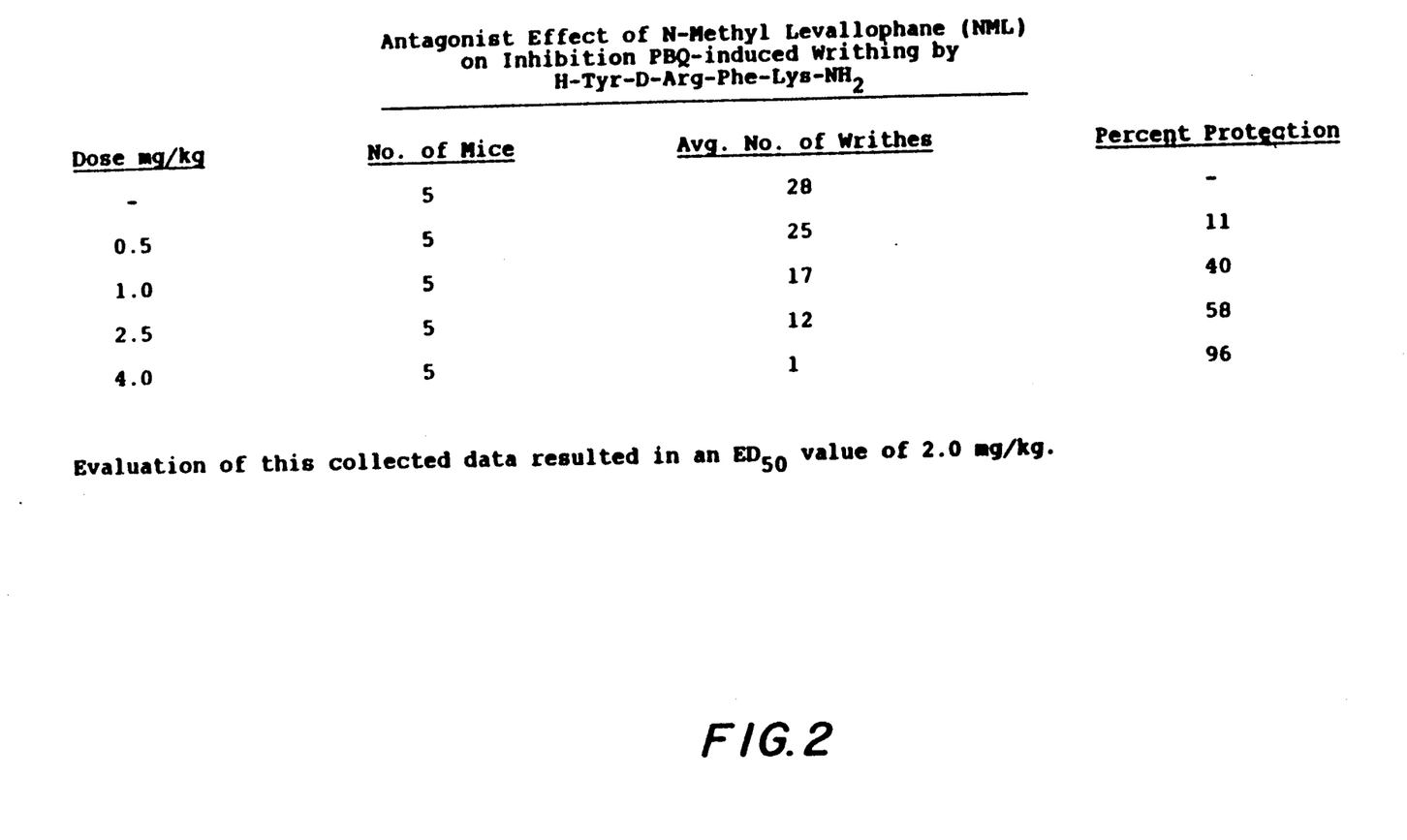
FIG. 2 is a table recording the antagonist effect of N-methyl levallophane (NML) on inhibition PBQ-induced writhing by H-Tyr-D-Arg-Phe-Lys-NH$_2$.
Figure 3:
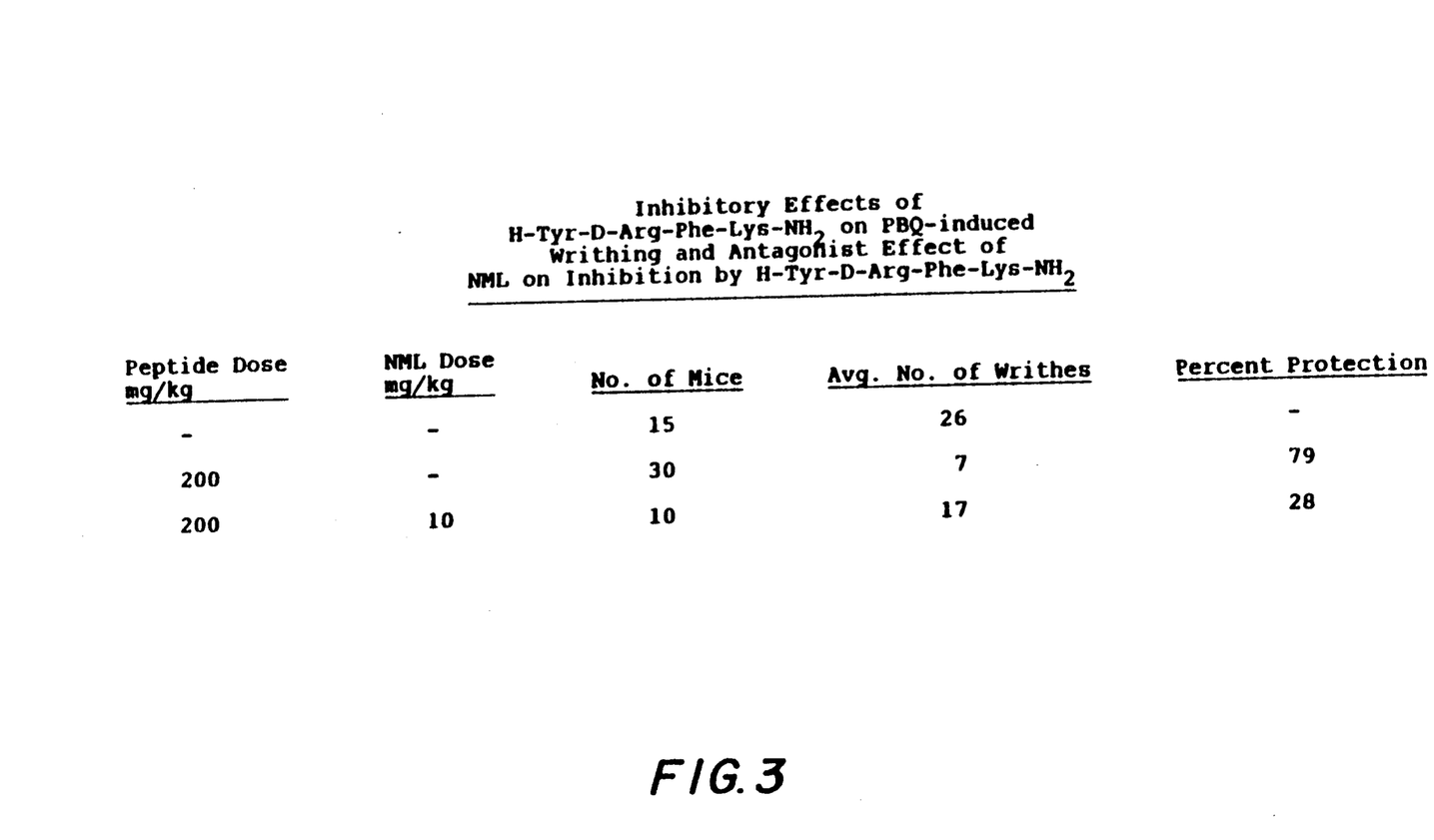
FIG. 3 is a table demonstrating the inhibitory effect of H-Tyr-D-Arg-Phe-Lys-NH$_2$ on PBQ-induced writhing and antagonist effect of NML on inhibition by H-Tyr-D-Arg-Phe-Lys-NH$_2$.

The anti-nociceptive effects of H-Tyr-D-Arg-Phe-Lys-$NH_2$ were antagonized by a prior intraperitoneal administration of 10 mg/kg of N-methyl levallorphan (NML), a peripheral opioid antagonist. In the presence of this antagonist, the analgesic $ED_{50}$ of H-Tyr-D-Arg-Phe-Lys-$NH_2$ was increased from 0.6 mg/kg (see FIG. 1, infra) to 2.0 mg/kg (FIG. 2 infra). This increase represented a 3.4 fold increase in the $ED_{50}$ value. It is known that quaternary salts of opioid anagonists, such as NML, do not penetrate the blood-brain barrier. They have been reported to merely produce a peripheral antagonist effect. Contrastingly, in a similar study, NML did not antagonize morphine—which is known to produce its analgesic effect from an interaction with opioid receptors in the brain.

Analysis of H-Tyr-D-Arg-Phe-Lys-$NH_2$ utilizing a mouse hot-plate, an assay which only detects sensory induced analgesic effects, established an $ED_{50}$ of 24 mg/kg. This illustrated that the peptide was forty times less active under these conditions than when analyzed in the PBQ writhing test. For experimental protocol with the hot-plate assay, see G. Woolfe and A. Mac-Donald, "The Evaluation of the Analgesic Action of Pethidine Hydrochloride (Demoral)", *J. Pharmacol. Exp. Ther.*, 80, p. 300 (1944). In a similar analysis performed on morphine, a decrease of only five fold was observed from the PBQ test to the thermal induction test. See R. Follenfant et al., supra. This loss of activity for H-Tyr-D-Arg-Phe-Lys-$NH_2$ indicates that a higher degree of peripherally mediated analgesic effectiveness is possessed by this peptide.

Oral analgesic activity was observed for Tyr-D-Arg-Phe-Lys-$NH_2$ at a dosage of 200 mg/kg. This analgesic activity was observed to be antagonized by NML, as reflected in Table 3 infra, and, thus, the activity was demonstrated to be of a peripheral nature.

EXAMPLE 3

Bioassays and Binding Assays

Opioid receptor affinities of peptides according to this invention were determined by displacement of selective radioligands from rat brain membrane preparations. These studies were performed in accordance with the procedures outlined in Schiller et al., *Biochem. Biophys. Res. Commun.*, 85, p. 1332 (1978). [$^3H$]DAGO and [$^3H$]DSLET, at 0.72 and 0.78 nM, respectively, served as radioligands, and incubations were performed at 0° C. for 2 hours. In vitro opioid activities of the peptides disclosed herein were determined based on inhibition of electrically evoked contractions of the guinea pig ileum (GPI) and the mouse vas deferens (MVD). The GPI assay is representative for $\mu$ receptor interactions, even though the ileum also contains $\kappa$ receptors. The $\kappa$ receptor interactions are characterized by relatively high $K_e$ values for naloxone as an antagonist (20-30 nM), in contrast to the low $K_e$ values (1-2 nM) observed with $\mu$ receptor ligands. In the MVD assay, opioid effects are primarily mediated by $\delta$ receptors, although $\mu$ and $\kappa$ receptors also exist in this tissue. $K_e$ values for naloxone as an antagonist were determined with the GPI preparation but not in the MVD assay due to the very low potency shown by all of these peptides on the vas deferens.

The GPI and MVD bioassays were carried out following the protocol described in Schiller et al. supra and DiMaio et al., *J. Med. Chem.* 25, p. 1432 (1982). A log dose—response curve was constructed with leu-enkephalin utilized as a standard for each ileum and vas deferens preparation. $IC_{50}$ values were obtained for the tested peptides by utilizing the Cheng and Prusoff equation, where 1.3 and 2.6 nM were used for the dissociation constants of [$^3H$]DAGO and $^3H$]DSLET, respectively. These values were then normalized. The $K_e$ values for naloxone as an antagonist were determined from the ratio of $IC_{50}$ values obtained in the presence of a fixed naloxone concentration and then in the absence of a fixed naloxone concentration.

In the [$^3H$]DAGO binding assay, H-Tyr-D-Nva-Phe-Orn-$NH_2$, while carrying a net charge of 2+ and showing about eight times higher $\mu$-receptor affinity than leu-enkephalin, its $\delta$-receptor affinity relative to the latter peptide was nearly 1000 times lower, as determined in the [$^3H$]DSLET binding assay. These results indicate that this peptide displays excellent $\mu$-receptor selectivity, as indicated by the very high ratio of the binding inhibition constant determined at the $\delta$- and the $\mu$-receptor ($K_i^\delta/K_i^\mu = 1880$). Reduction of the net positive charge by one unit through substitution of asparagine for ornithine in position 4 produced a ten-fold decrease in $\mu$-receptor affinity and a five-fold increase in $\delta$-receptor affinity. Therefore, by carrying a net charge of 1+, only a moderate preference for $\mu$-receptors over $\delta$-receptors ($K_i^\delta/K_i^\mu = 37.7$) is demonstrated. Lengthening the side chain in position 2, by the substitution of norleucine, did not appreciably affect the receptor binding affinity and selectivity.

Analogs containing a D-arginine residue in position 2 and a second basic residue in position 4, carried a further increased net positive charge of 3+. These analogs retained similarly high affinity for the μ-receptor but displayed even lower δ-receptor affinity.

The most selective peptide was H-Tyr-D-Arg-Phe-Lys-NH₂ with a $K_i^\delta/K_i^\mu$ ratio of 11400. This peptide is ten times more μ-selective than DAGO ($K_i^\delta/K_i^\mu = 1050$) which hitherto had generally been regarded as one of the most selective μ-agonists available.

The receptor binding profiles of these opioid peptide analogs are consistent with the membrane compartment concept discussed in Schwyzer, supra. Augmenting the positive charge from 1+ to 2+ or 3+ resulted in higher μ-receptor affinity, possibly, but not necessarily, due to the increased accumulation of the peptides carrying a high positive charge in the anionic fixed-charge compartment of the membrane—where μ-receptors are thought to be located. On the other hand, the gradual augmentation of the positive charge within this series of compounds leads to a progressive decrease in δ-receptor affinity. This is presumably due to the increasing electrostatic repulsion in the positively charged aqueous compartment which, according to the membrane compartment concept, contains δ-receptors.

The $IC_{50}(MVD)/IC_{50}(GPI)$ ratios obtained were generally considerably lower than the corresponding $K_i^\delta/K_i^\mu$ ratios determined in the binding assays described herein. This was illustrated with peptides of the present invention due to the fact that many of these peptides showed higher potencies in the MVD assay than was expected on the basis of the δ-receptor affinities determined in the [³H]DSLET binding assay and relatively lower potencies in the GPI assays in relation to the measured μ-receptor affinities in the [³H]DAGO binding assay. The unexpectedly high potencies of many of these opioid peptide analogs in the NVD assay are possibly, but not necessarily, due to additional interactions with μ-receptors which are also found in the vas deferens. The relatively lower potencies in the GPI assay may be the result of a somewhat lower "efficacy" at the μ-receptor. Alternatively, these discrepancies between binding assay and bioassay data may be due to a different degree of nonspecific adsorption of these highly charged molecules in the various tissues.

Figure 6:
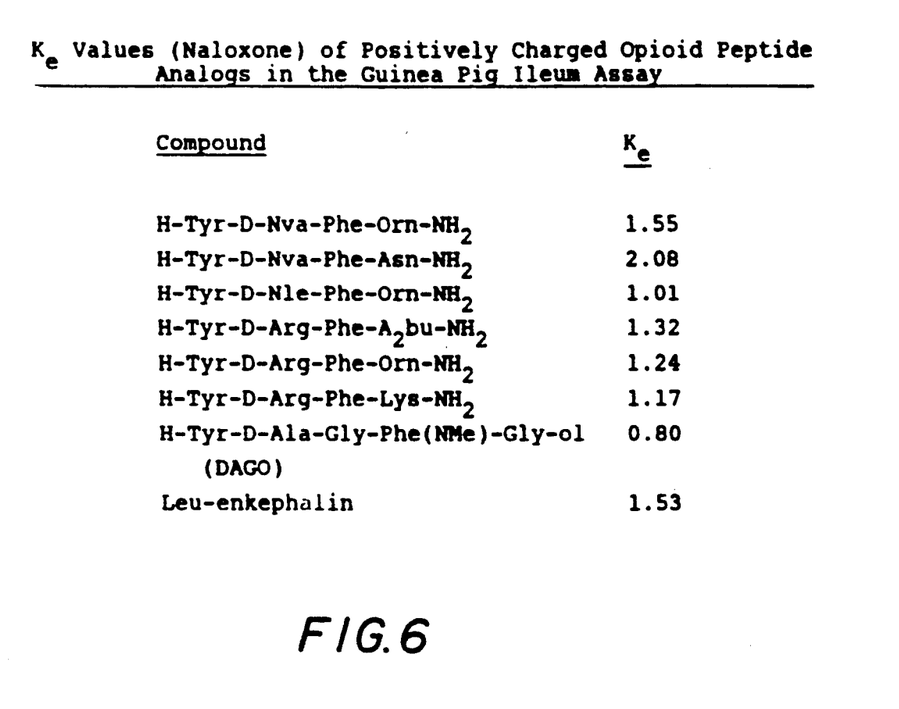
FIG. 6 is a table displaying the K$_e$ values (naloxone) of positively charged opioid peptide analogs in the guinea pig ileum assay.

Low $K_e$ values, as illustrated in FIG. 6 infra, are typical for μ-receptor interactions and rule out an additional interaction with κ-receptors on the ileum, since κ-receptor interactions would demonstrate much higher $K_e$ values.

The most selective among the opioid peptide analogs, H-Tyr-D-Arg-Phe-Lys-NH₂, showed extremely high preference for μ-receptors over δ-receptors, being more than 10 times as μ-selective as DAGO. On the basis of the extremely high receptor selectivity ratio ($K_i^\delta/K_i^\mu = 11,400$) observed with H-Tyr-D-Arg-Phe-Lys-NH₂, it may be concluded that this compound represents the most selective μ-agonist reported to date.

Because of its high positive charge, H-Tyr-D-Arg-Phe-Lys-NH₂ most likely will not be unable to cross the blood-brain barrier to any significant extent. It may thus be the case that, aside from its high μ-receptor preference, this analog may also show pronounced selectivity for peripheral versus central receptors.

Figure 4:
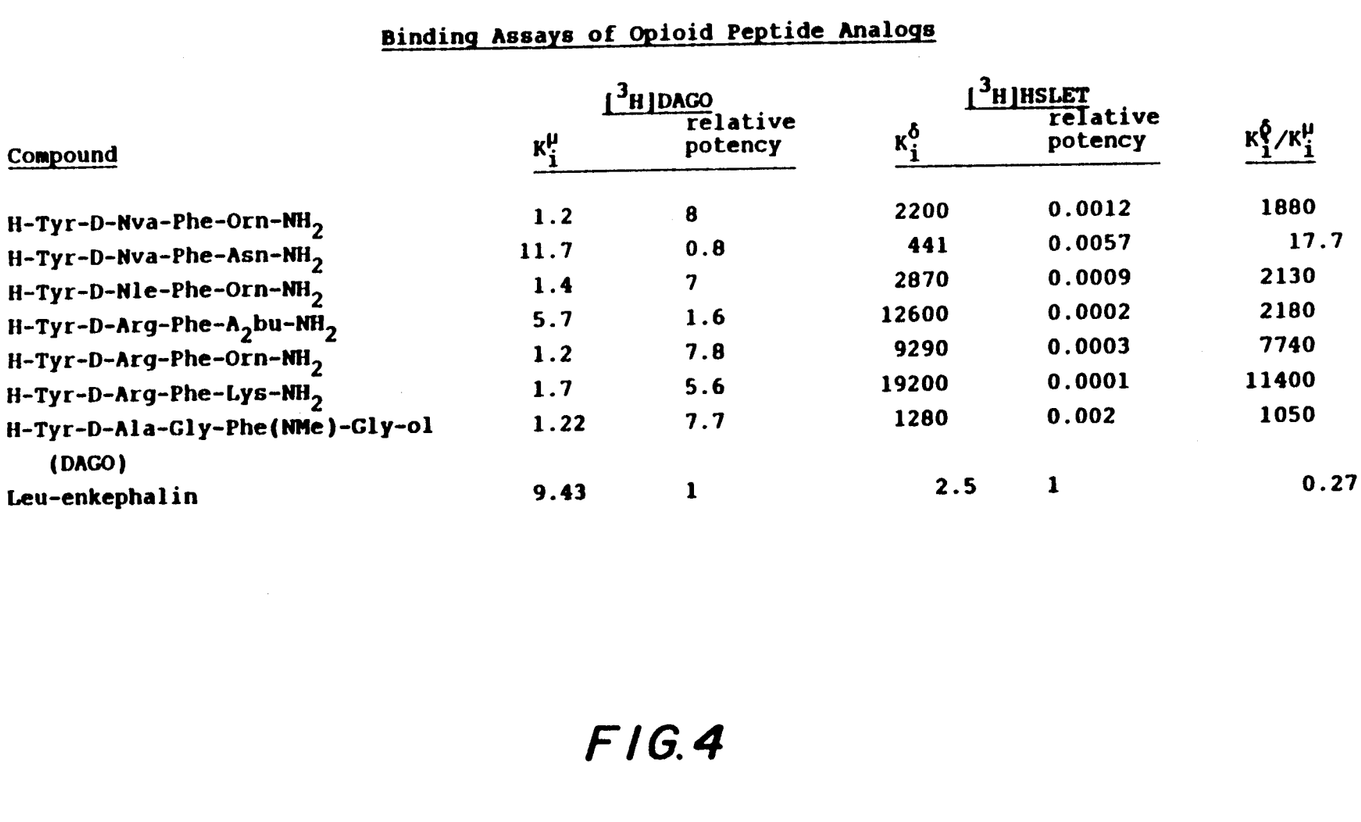
FIG. 4 is a table illustrating the data obtained from the binding assays of opioid peptide analogs which yields their ratios of binding constant inhibition.
Figure 5:
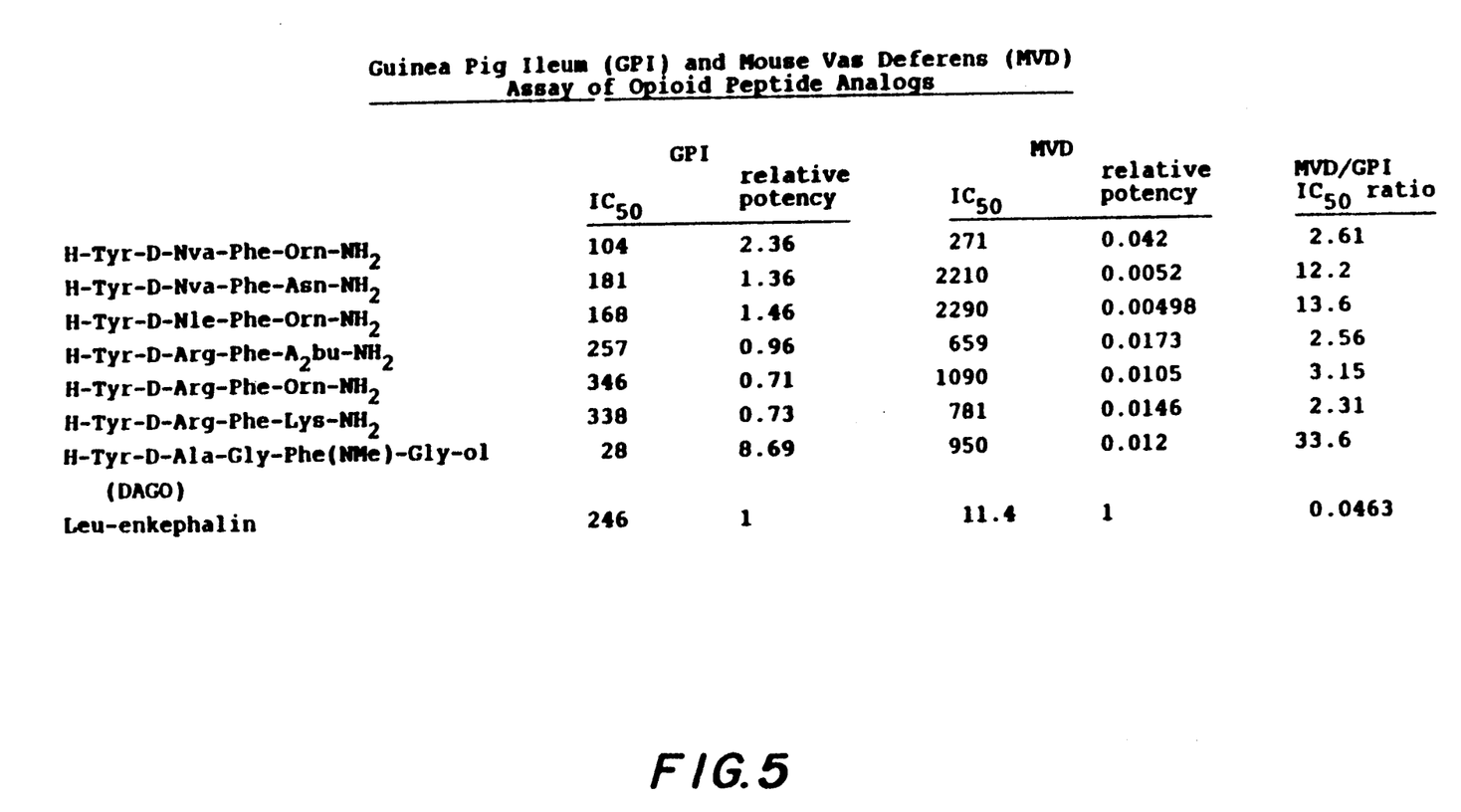
FIG. 5 is a table exhibiting the data obtained from the guinea pig ileum and mouse vas deferens assay of opioid peptide analogs which affords their ratios of binding constant inhibition.

The foregoing examples are further demonstrated by the values recorded in FIGS. 4, 5, and 6, infra.

In order that the invention described herein may be more fully understood, the following examples are set forth. It should be understood that these examples are for illustrative purposes only and are not to be construed as limiting this invention in any manner.

What is claimed is:

1. A peptide represented by the formula:

2. A peptide represented by the formula:

3. A peptide represented by the formula:

4. A peptide represented by the formula:

5. A peptide represented by the formula:

* * * * *